(12) United States Patent
DeWitte et al.

(10) Patent No.: US 9,236,236 B2
(45) Date of Patent: Jan. 12, 2016

(54) SYSTEM LAYOUT FOR AN AUTOMATED SYSTEM FOR SAMPLE PREPARATION AND ANALYSIS

(71) Applicant: Thermo Fisher Scientific Oy, Vantaa (FI)

(72) Inventors: Robert DeWitte, Burlington (CA); Juhani Siidorov, Vantaa (FI); Vesa Nuotio, Espoo (FI); Jukka Saukkonen, Espoo (FI); John Edward Brann, III, Shrewsbury, MA (US); Terry N. Olney, Tracy, CA (US)

(73) Assignee: Thermo Fisher Scientific Oy, Vantaa (FI)

( * ) Notice: Subject to any disclaimer, the term of this patent is extended or adjusted under 35 U.S.C. 154(b) by 0 days.

(21) Appl. No.: 14/333,724

(22) Filed: Jul. 17, 2014

(65) Prior Publication Data
US 2015/0056689 A1    Feb. 26, 2015

Related U.S. Application Data

(62) Division of application No. 13/882,399, filed as application No. PCT/US2011/058323 on Oct. 28, 2011, now Pat. No. 9,000,360.

(60) Provisional application No. 61/408,180, filed on Oct. 29, 2010.

(51) Int. Cl.
*H01J 49/26* (2006.01)
*H01J 49/10* (2006.01)
(Continued)

(52) U.S. Cl.
CPC .............. *H01J 49/10* (2013.01); *G01N 27/62* (2013.01); *G01N 30/06* (2013.01); *G01N 30/72* (2013.01); *G01N 30/7233* (2013.01); *G01N 30/8658* (2013.01); *G01N 35/0092* (2013.01); *G01N 35/00871* (2013.01); *G01N 35/026* (2013.01);
(Continued)

(58) Field of Classification Search
USPC .......................................... 250/281, 282, 288
See application file for complete search history.

(56) References Cited

U.S. PATENT DOCUMENTS

| 4,570,068 A | 2/1986 | Sakairi et al. |
| 4,854,181 A | 8/1989 | Gerstel |

(Continued)

FOREIGN PATENT DOCUMENTS

| EP | 0345782 A2 | 12/1989 |
| WO | 0184143 A1 | 11/2001 |

(Continued)

OTHER PUBLICATIONS

International Searching Authority, Preliminary Report on Patentability and Written Opinion in related Application No. PCT/US2011/058452, dated Apr. 30, 2013 (15 pages).

(Continued)

*Primary Examiner* — Nicole Ippolito
(74) *Attorney, Agent, or Firm* — Wood, Herron & Evans, LLP

(57) ABSTRACT

A sample preparation and analysis system. The system includes a housing with a sample preparation station and a sample analysis station positioned within the housing. The sample analysis station is spaced away from the sample preparation station. A transport assembly is configured to move at least one sample within the housing and between the sample preparation station and the sample analysis station.

20 Claims, 6 Drawing Sheets

(51) Int. Cl.
*G01N 30/06* (2006.01)
*G01N 30/72* (2006.01)
*G01N 30/86* (2006.01)
*G01N 35/00* (2006.01)
*G01N 35/02* (2006.01)
*G01N 35/08* (2006.01)
*G01N 27/62* (2006.01)
*H01J 49/04* (2006.01)
*G01N 30/88* (2006.01)
*H01J 49/00* (2006.01)

(52) U.S. Cl.
CPC ............ *G01N 35/08* (2013.01); *H01J 49/0031* (2013.01); *H01J 49/0413* (2013.01); *G01N 2030/8804* (2013.01); *H01J 49/00* (2013.01); *H01J 49/0409* (2013.01); *H01J 49/0431* (2013.01); *Y10T 436/24* (2015.01)

(56) References Cited

U.S. PATENT DOCUMENTS

| | | | |
|---|---|---|---|
| 4,883,504 A | 11/1989 | Gerstel | |
| 5,065,614 A | 11/1991 | Hartman et al. | |
| 5,313,061 A | 5/1994 | Drew et al. | |
| 5,789,746 A | 8/1998 | Kato et al. | |
| 6,054,683 A | 4/2000 | Bremer et al. | |
| 6,055,845 A | 5/2000 | Gerstel et al. | |
| 6,134,945 A | 10/2000 | Gerstel et al. | |
| 6,180,410 B1 | 1/2001 | Gerstel et al. | |
| 6,245,298 B1 | 6/2001 | Bremer et al. | |
| 6,354,136 B1 | 3/2002 | Bremer et al. | |
| 6,360,588 B1 | 3/2002 | Ross et al. | |
| 6,447,575 B2 | 9/2002 | Bremer et al. | |
| 6,475,437 B1 | 11/2002 | Gerstel et al. | |
| 6,730,517 B1 | 5/2004 | Köster et al. | |
| 6,743,397 B1 | 6/2004 | Zesiger | |
| 6,761,056 B2 | 7/2004 | Schram et al. | |
| 6,815,216 B2 | 11/2004 | Sandra et al. | |
| 6,858,435 B2 | 2/2005 | Chervet et al. | |
| 6,907,796 B2 | 6/2005 | Bremer et al. | |
| 6,973,846 B2 | 12/2005 | Bremer et al. | |
| 7,127,956 B2 | 10/2006 | Bremer et al. | |
| 7,157,055 B2 | 1/2007 | Rose | |
| 7,178,414 B1 | 2/2007 | Kokosa | |
| 7,530,258 B2 | 5/2009 | Bremer et al. | |
| 7,603,201 B2 | 10/2009 | Feingold et al. | |
| 7,712,385 B2 | 5/2010 | Bremer et al. | |
| 7,939,310 B2 | 5/2011 | Ginns et al. | |
| 2001/0027722 A1 | 10/2001 | Bremer et al. | |
| 2002/0098594 A1 | 7/2002 | Sandra et al. | |
| 2002/0137194 A1 | 9/2002 | Ammann et al. | |
| 2002/0155587 A1 | 10/2002 | Opalsky et al. | |
| 2003/0068825 A1 | 4/2003 | Washburn et al. | |
| 2003/0124539 A1 | 7/2003 | Warrington et al. | |
| 2003/0180185 A1 | 9/2003 | Rose | |
| 2003/0233893 A1 | 12/2003 | Bremer et al. | |
| 2004/0158433 A1 | 8/2004 | Wimschneider et al. | |
| 2004/0159167 A1 | 8/2004 | Bremer et al. | |
| 2005/0032237 A1 | 2/2005 | Sandra et al. | |
| 2005/0194318 A1 | 9/2005 | Ozbal et al. | |
| 2005/0229723 A1 | 10/2005 | Bremer et al. | |
| 2005/0288183 A1 | 12/2005 | Sandra et al. | |
| 2006/0226358 A1 | 10/2006 | Ishikawa et al. | |
| 2007/0137320 A1 | 6/2007 | Bremer et al. | |
| 2007/0140904 A1 | 6/2007 | Bremer et al. | |
| 2008/0089809 A1 | 4/2008 | Gerstel et al. | |
| 2008/0314129 A1 | 12/2008 | Schultz et al. | |
| 2009/0247417 A1* | 10/2009 | Haas ..................... G01N 33/15 506/8 |
| 2011/0157580 A1 | 6/2011 | Nogami et al. | |
| 2013/0056631 A1 | 3/2013 | Tomany et al. | |

FOREIGN PATENT DOCUMENTS

| | | |
|---|---|---|
| WO | 03049831 A2 | 6/2003 |
| WO | 2005009202 A2 | 2/2005 |
| WO | 2006038014 A1 | 4/2006 |
| WO | 2006089103 A1 | 8/2006 |

OTHER PUBLICATIONS

International Searching Authority, Preliminary Report on Patentability and Written Opinion in corresponding Application No. PCT/US2011/058323, dated Apr. 30, 2013 (18 pages).

International Searching Authority, International Search Report and Written Opinion in related Application No. PCT/US2011/058452, dated Mar. 23, 2012 (26 pages).

Gerstel, Maestro Software, product brochure, date unknown (4 pages).

International Property Office of Singapore, Singapore Search Report and Written Opinion in corresponding patent application No. 201303312-1, mailed Jul. 21, 2014 (20 pages).

* cited by examiner

SYSTEM LAYOUT FOR AN AUTOMATED SYSTEM FOR SAMPLE PREPARATION AND ANALYSIS

CROSS-REFERENCE TO RELATED APPLICATION

This application is a divisional of co-pending U.S. patent application Ser. No. 13/882,399, filed Jul. 17, 2013, which is a submission under 35 U.S.C. §371 of International Application No. PCT/US2011/058323, filed Oct. 28, 2011, which claims the filing benefit of U.S. Provisional Application Ser. No. 61/408,180, filed Oct. 29, 2010, the disclosures of which are hereby expressly incorporated by reference herein in their entireties.

FIELD OF THE INVENTION

The present invention relates generally to the field of sample preparation and analysis and, more particularly, to systems and layouts for arranging sample preparation and analysis instrumentations.

BACKGROUND OF THE INVENTION

Liquid chromatography mass spectrometry ("LCMS") is a powerful analyte detection and measurement technique that has become the preferred method of detecting small molecule, amino acid, protein, peptide, nucleic acid, lipid, and carbohydrate analytes to a high accuracy for diagnostic purposes. However, the instrumentation required for LCMS is technically complex and not well suited to the typical hospital clinical lab or medical lab technician. These clinical labs have not adopted LCMS diagnostics and, instead, generally use alternative diagnostic techniques, including automated immunoassay. Alternatively, the clinical labs may send the samples out to a central laboratory for analysis.

Therefore, there is a need for sample preparation and sample analysis systems that are less complex to configure and use for preparing samples and conducting a variety of different analyte assays, without requiring the expertise of LCMS technologists, or the massive scale of a reference laboratory. There is yet also a need for a sample preparation and sample analysis systems that improve the efficiency of the time to result for a variety of different analyte assays.

SUMMARY OF THE INVENTION

The present invention overcomes the foregoing problems and other shortcomings, drawbacks, and challenges of conventional sample preparation and sample analysis systems. While the invention will be described in connection with certain embodiments, it will be understood that the invention is not limited to these embodiments. To the contrary, this invention includes all alternatives, modifications, and equivalents as may be included within the spirit and scope of the present invention.

In accordance with one embodiment of the present invention, a sample preparation and analysis system includes a housing. A sample preparation station and a sample analysis station are positioned within the housing and with the sample analysis station is spaced away from the sample preparation station. A transport assembly is configured to move at least one sample within the housing and between the sample preparation station and the sample analysis station.

According to another embodiment of the present invention, an automated biological specimen preparation and mass spectrometry analysis system includes a sample preparation station and a sample analysis station. The sample preparation station is configured to prepare samples that are taken from a plurality of biological specimens. The sample analysis station includes a mass spectrometer that is configured to quantify one or more analytes in the prepared samples. The sample preparation and the sample analysis stations are contained within a housing such that the mass spectrometer is lower than the sample analysis station.

According to yet another embodiment of the present invention, an automated biological specimen preparation and analysis system includes a sample preparation station and a sample analysis station. The sample preparation station is configured to prepare samples that are taken from a plurality of biological specimens and includes a first serviceable component, which may include a specimen rack and/or a reagent rack. The sample analysis station configured to quantify one or more analytes in the prepared samples and including a second serviceable component, which may include a liquid chromatography column and/or a liquid chromatography mobile phase container. A third serviceable component includes a fluid container and/or a waste container. The sample preparation station, the sample analysis station, and the third serviceable component are contained within a housing such that the first, second, and third serviceable components are positioned closer to a front face of the housing than to a back face of the housing.

Still another embodiment of the present invention is directed to an automated biological specimen preparation and analysis system and includes a sample preparation station and a sample analysis station. The sample preparation station is configured to prepare samples that are taken from a plurality of biological specimens. The sample analysis station is configured to quantify one or more analytes in the prepared samples. A user interface is configured to receive and/or convey information to a user. A housing contains the sample preparation and sample analysis stations. The user interface s mounted to an exterior portion of the housing and positioned between a left-hand sidewall and a right-hand sidewall of the housing.

According to another embodiment of the present invention, an automated biological specimen preparation and analysis system includes sample preparation and sample analysis stations positioned within a housing. The sample preparation station is configured to prepare samples taken from patient specimen. The samples are prepared in accordance with an assay selected from a database containing a plurality of unique assays. The sample analysis station includes an analyzer that is dynamically reconfigurable according to the selected assay. Once dynamically reconfigured, the analyzer analyzes the prepared sample. A transport mechanism is configured to transport the prepared sample within the housing and from the sample preparation station to the sample analysis station.

The above and other objects and advantages of the present invention shall be made apparent from the accompanying drawings and the descriptions thereof.

BRIEF DESCRIPTION OF THE FIGURES

The accompanying drawings, which are incorporated in and constitute a part of this specification, illustrate embodiments of the invention and, together with the general description given above and the detailed description of the embodiments given below, serve to explain the principles of the present invention. In the figures, corresponding or like numbers or characters indicate corresponding or like structures.

DETAILED DESCRIPTION OF THE INVENTION

Figure 1A:
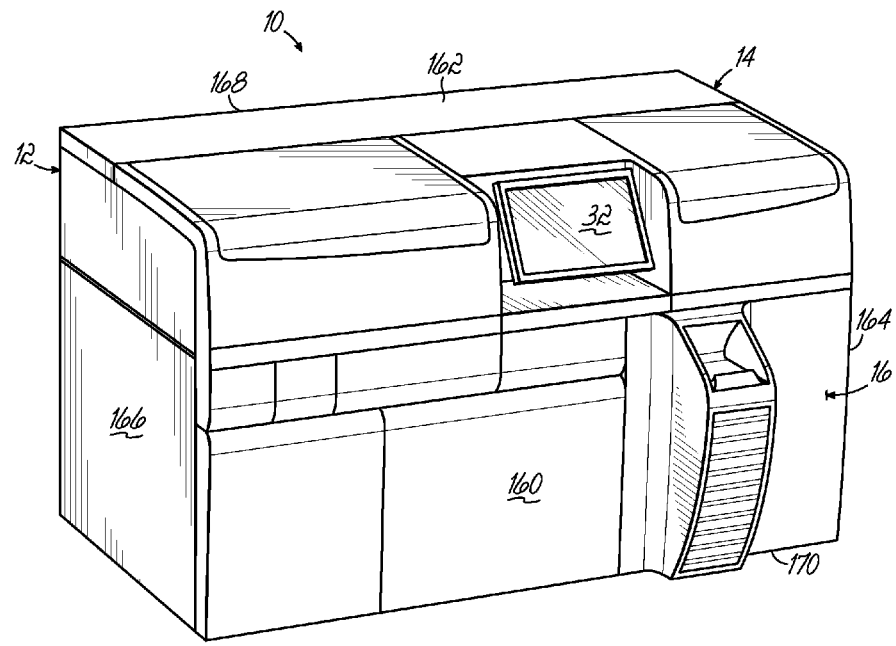
FIG. 1A is a perspective view of an automated sample preparation and analysis system in accordance with one embodiment of the present invention.

FIG. 1A is a perspective illustration of an automated sample preparation and analysis system 10 according to one exemplary embodiment of the present invention (referred to hereinafter as "system" 10). The system 10 is designed to automatically prepare a sample from a specimen for analysis and to analyze the prepared sample according to a predetermined analyte assay selected from a variety of different or unique analyte assays. As will be described in greater detail below, the exemplary system 10 is particularly designed to perform two distinct laboratory functions, i.e., sample preparation and sample analysis, in combination in an automated system.

In one embodiment, the system 10 includes a sample preparation station 12 for preparing various samples and a sample analysis station 14, which includes a suitable analyzer, such as a liquid chromatography mass spectrometer ("LCMS"), a gas chromatography mass spectrometer ("GCMS"), a surface desorption/ionizer directly coupled to a mass spectrometer; a liquid chromatography ultra-violet spectrometer ("LC/UV-VIS"), or a fluorescence spectrometer, for example, for analyzing the prepared samples according to selected analyte assays. The sample preparation station 12 and the sample analysis station 14 are interconnected in an automated manner as will be described in detail below and may, in fact, be enclosed within a unitary cover 16.

The unitary cover 16 is designed to be compartmental, permitting relative isolation of each station 12, 14. For example, according to the exemplary system depicted in FIG. 1A, the unitary cover 16 is formed of metal partitions and includes separate compartments for each of the sample preparation station 12 and the sample analysis station 14, for example, any associated liquid chromatography pumps, a centrifuge rotor, one or more power units, controllers 21, 23, mobile phase containers 128, and waste containers 70.

Figure 1B:
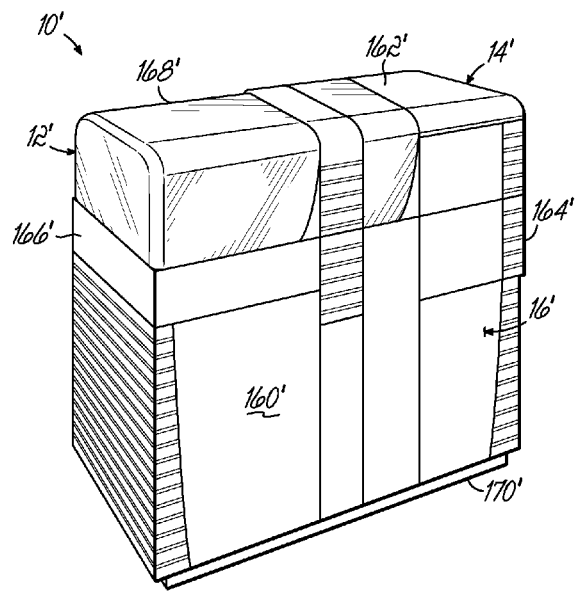
FIG. 1B is a perspective view of an automated sample preparation and analysis system in accordance with another embodiment of the present invention.

FIG. 1B, like FIG. 1A is a perspective illustration of an automated sample preparation and analysis system 10' and were similar numbers with primes refer to similar features.

Figure 2A:
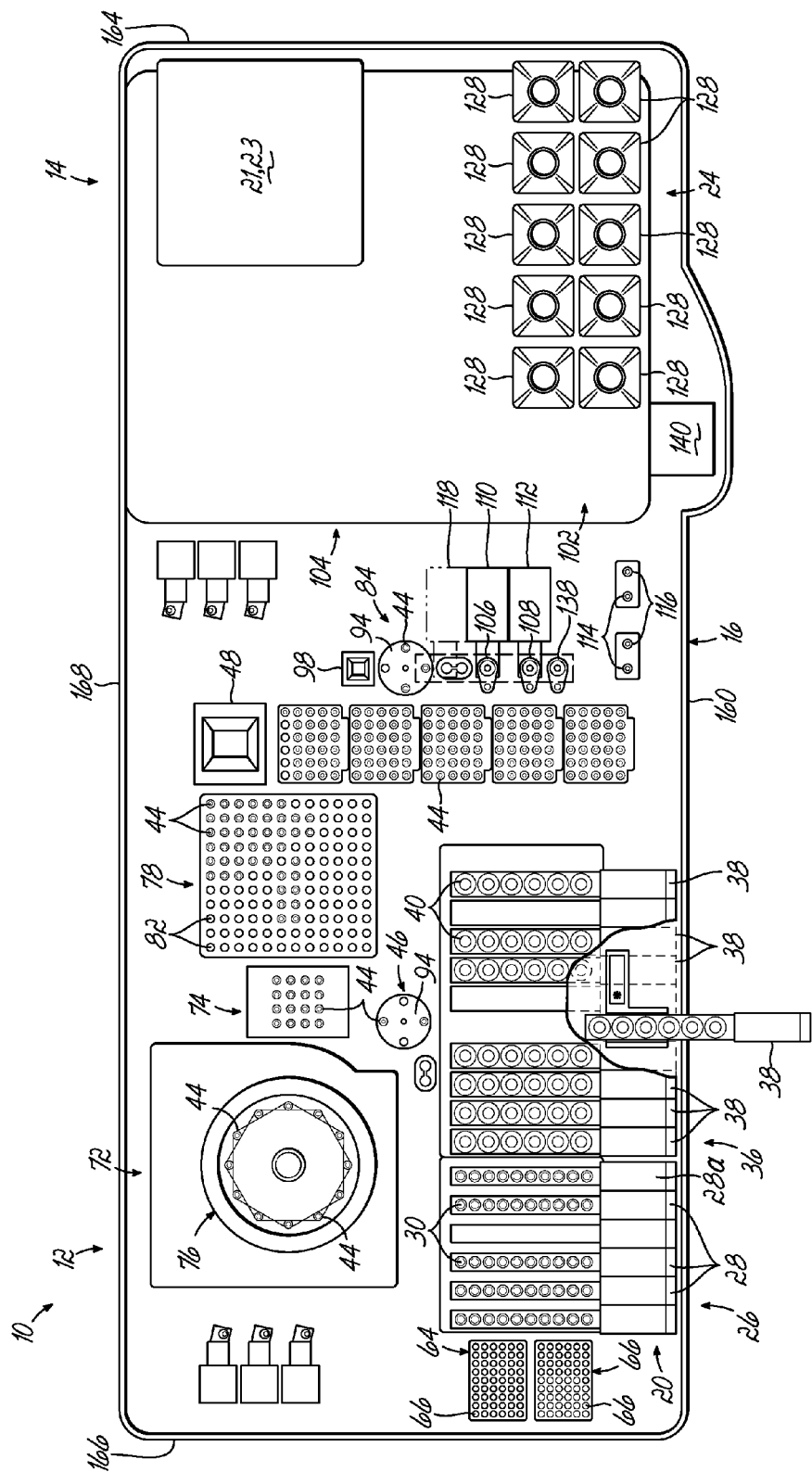
FIG. 2A is a top view of the automated sample preparation and analysis system of FIG. 1A.
Figure 2B:
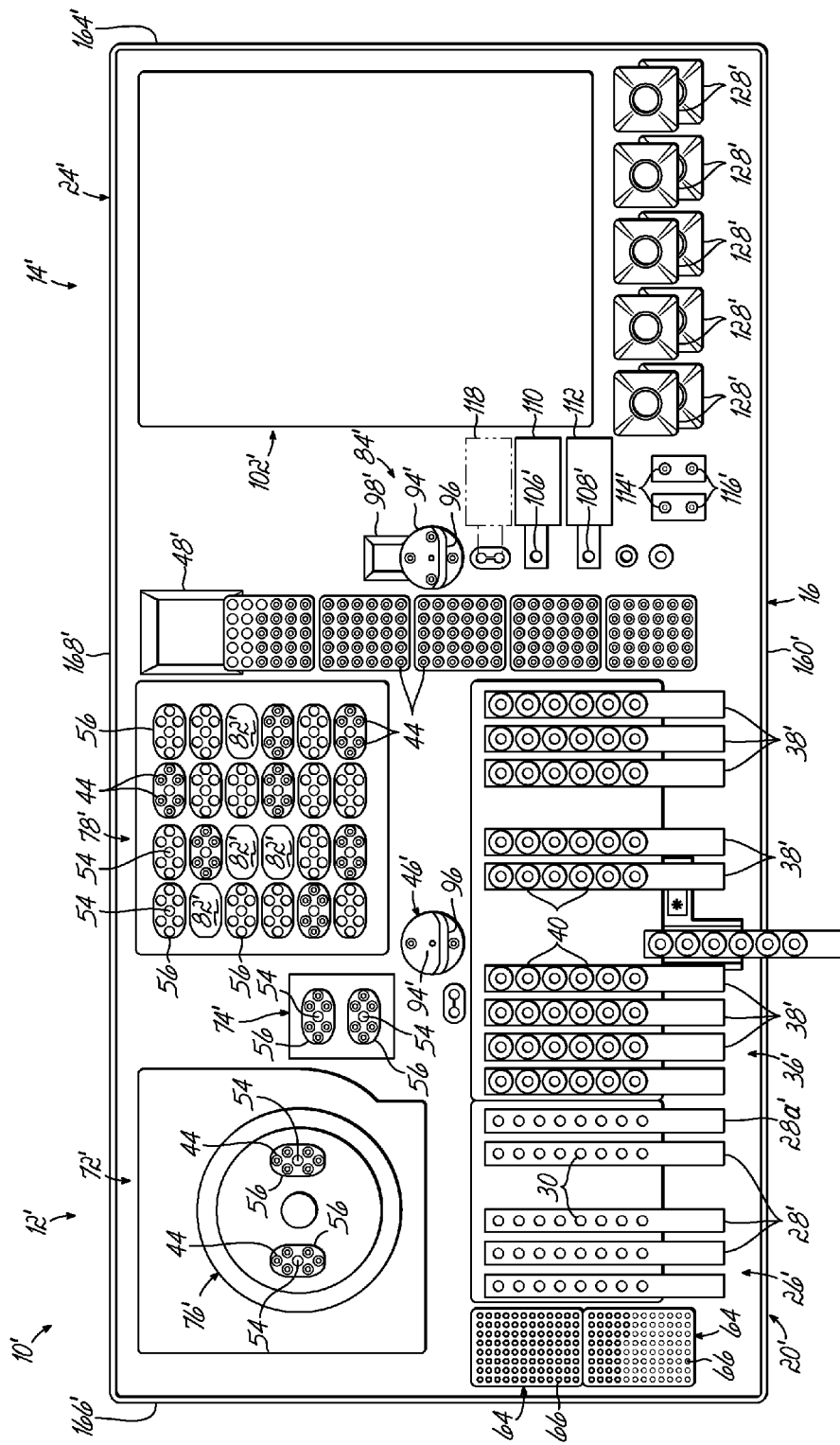
FIG. 2B is a top view of the automated sample preparation and analysis system of FIG. 1B.

Referring still to FIGS. 1A and 1B and now also to FIGS. 2A and 2B, the sample preparation station 12 of the system 10 may include a sample preparation station 20 and a sample preparation controller 21 that controls selected functions or operations of the sample preparation station 20. The sample preparation station 20 is configured to receive one or more specimens, to sample the specimens to prepare the samples for analysis according to a variety of preselected analyte assays, and to transport the prepared samples for analysis to the sample analysis station 14. In some embodiments, the sample preparation station 20 is configured to prepare the sample such that the prepared sample is chemically compatible with the sample analysis station 14 according to the selected analyte assay to be performed by the sample analysis station 14.

The sample analysis station 14, in like manner, includes a sample analysis station 24 and a sample analysis controller 23 that controls selected functions or operations of the sample analysis station 24. The sample analysis station 24 is configured to receive the prepared sample from the sample preparation station 20 via a transport mechanism described in greater detail below. The sample analysis station 24 then analyzes the prepared sample according to a selected analyte assay to obtain a result for that sample. The sample result may be transmitted to the sample preparation controller 21, which may validate the results.

While not specifically shown, a general controller may be used to control the sample preparation controller 21 and the sample analysis controller 23 or, alternatively, the sample analysis controller 23 may be made a slave to the master sample preparation controller 21, or vice versa. Further, while the designation of the sample preparation controller 21 and the sample analysis controller 23 as provided herein seems to indicate that the sample preparation station 20 and the sample analysis station 24 comprise two opposing sides of the system 10, the stations 12, 14 may encompass the same area or footprint. Indeed, in accordance with the present invention, in some embodiments the sample preparation station 20 and the sample analysis station 24 need not be encompassed within the same housing or unit.

The sample preparation station 20 includes a specimen dock 26 having one or more specimen racks 28. Each specimen rack 28 includes one or more specimen rack positions capable of holding a specimen container 30. The specimen containers 30 are configured to contain the acquired biological or environmental specimens, which may be any specimen containing or suspected of containing an analyte of interest. These patient specimens or environmental samples may be analyzed for one or more analytes, which may include, but are not limited to, drugs, pro-drugs, metabolites of drugs, metabolites of normal biochemical activity, peptides, proteins, antibiotics, metabolites of antibiotics, toxins, microorganisms (including bacteria, fungi, and parasites), and infectious agents (including viruses and prions). Further, any of the foregoing samples, alone or in combination, may be suspended in an appropriate media, for example, within a blood culture or a screening booth.

The specimen container 30, itself, may include any suitable labware, such as a vessel, a vial, a test tube, or any other suitable container known in the art. One or more of the specimen racks 28 may be designated, or otherwise labeled (e.g., by placement of the rack 28 within the sample preparation station 20 or with a barcode or an RFID antenna), as priority racks 28a, or STAT, for introducing specimen containers 30 having urgent specimens. The sample preparation station 20 further includes a reagent station 36 containing multiple reagent racks 38. Each reagent rack 38 includes one or more reagent rack positions capable of holding one or more reagent containers 40 that contain solvents and/or reagents, some of which may be comprised of a volatile liquid.

A touch screen display 32 or other similar user interface is positioned on the upper half of the system 10 and in a central position of the housing 16. Placing the touch screen display 32 within the footprint of the system 10 rather than as a stand-alone computer or as an appendage attached to the side of the system 10 reduces the overall footprint of the system 10 and frees floor space in the laboratory environment. Given the overall length of the system 10, placement of the touch screen display 32 centrally reduces the maximum distance between the touch screen display 32 and each of the sample preparation station 12 and the sample analysis station 14. Reducing this distance, as much as possible, is advantageous for the user who needs to review messages provided on the touch screen display 32, for example, specimen addition or reagent replenishment instructions, while nearly simultaneously attending to the user serviceable components of the system 10, for example, adding specimen racks or new reagent containers to the system 10. Additionally, the touch screen display 32 is mounted in a manner to make the interface adjustable, both for height as well as for angle of incline, to optimize its position for each individual user.

A patient sample (referred to hereinafter as "sample"), or a portion of a particular specimen contained within a specimen container 30 is transferred to an open-top sample vessel 44 (also known as a reaction vessel, but referred to hereinafter as "vessel" 44) to be prepared for analysis. The vessels 44 may be stored within, and introduced from, a storage station (not shown) of the sample preparation station 20. Within the storage station, the vessels 44 may reside in plates (not shown) or other appropriate mass storage containers. As various ones of the vessels 44 are transferred and periodically leaving empty plates, the plates may be discarded through a waste chute 48 from the sample preparation station 20.

Figure 4:
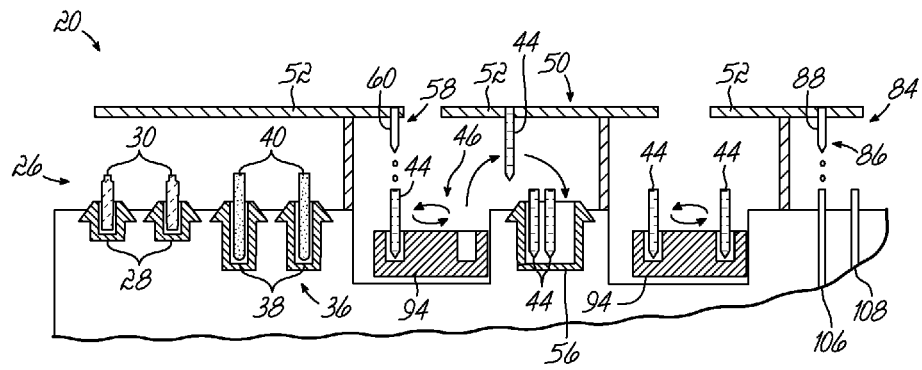
FIG. 4 is a schematic view of a sample preparation station and a transport assembly of the automated sample preparation and analysis system of FIG. 1A in accordance with one embodiment of the present invention.

When a specimen is sampled, one or more vessels 44 are transferred to a sampling station 46 from the storage station by way of a transport assembly 50 (FIG. 4). The transport assembly 50 (FIG. 4) may include a robot assembly operating on one or more tracks 52 and configured to move in at least one of an x-y direction, an x-y-z direction, or a rotary direction. An exemplary track system and associated transport bases are described in detail in co-owned U.S. Pat. No. 6,520,313, entitled "Arrangement and Method for Handling Test Tubes in a Laboratory," naming inventors Kaarakainen, Korhonen, Makela, and which is hereby incorporated by reference in its entirety herein.

The sampling station 46 may include a rotatable table 94 having a vessel cap opening and closing device 96 for opening and closing a hinged lid of the vessel, if present. One having ordinary skill in the art will appreciate that alternative embodiments of a transport mechanism to transport a portion of a particular specimen contained within a specimen container 30 to the vessel 44 may be used without departing from the scope of embodiments of the invention.

While not shown, the transport assembly 50 may further include a gripper, or other like device, to capture and release the vessel 44 or a transport handle 54 associated with a vessel rack 56, if used, to simultaneously transport two or more vessels 44 within the system 10.

In another embodiment, not shown, the transport assembly 50 may include a robot assembly configured to move in at least one of an x-y direction, an x-y-z direction, or a rotary direction and which may include an automated liquid handler. According to this embodiment, the automated liquid handler may aspirate and dispense a volume of a liquid between two or more vessels 44 within the system 10 to transport the liquid between two or more stations within the system 10.

In still other embodiments, the transport assembly 50 may further include carousels, i.e., a circular revolving disc, or autosamplers having multiple vessel positions therein to provide transport function and allow for a temporary, intermediate vessel storage function.

The transport assembly 50 may further comprise a sample pipette assembly 58 (FIG. 4) having a pipette shaft 60 (FIG. 4) that is movable, for example via a robotic device, in one or more of the x-y-z directions and between two or more of the specimen dock 26, the reagent station 36, and the sampling station 46.

The sample pipette assembly 58 may aspirate an aliquot of the specimen from the specimen container 30 from within the specimen dock 26 and dispense the aliquot of the specimen into the vessel 44 within the sampling station 46. Additionally, or alternatively, the sample pipette assembly 58 may aspirate an aliquot of a desired reagent from one of the reagent containers 40 within the reagent station 36 and dispense the aliquot of the desired reagent into the vessel 44 within the sampling station 46, which may or may not previously include the sample, i.e., the aliquot of the specimen.

According to still another embodiment, the sample is selected from a culture plate using a commercially-available colony picker instrument, for example, the PICKOLO (Tecan Group, Ltd., Männedorf, Switzerland) or the QPIX (Genetix, now part of Molecular Devices, San Jose, Calif.). The colony picker is capable of collecting an aliquot of the specimen 23 from a colony, optionally, a pre-selected or pre-designated colony, on a culture plate and depositing the sample into the vessel 44. The colony-containing vessel may then be mixed, as described above, to lyse the cells and denature the proteins in order to stabilize the sample for later microbial analysis.

The sample within the vessel 44 is transferred via the transport assembly 50 from the sampling station 46 to a secondary processing station 72. The secondary processing station 72 includes, for example, one or more of a mixing station 74, an incubation station, and a matrix interference removal station (shown specifically herein as a centrifuge 76).

The matrix interference removal station, if included within the secondary processing station 72, may be incorporated in either of an on-line or off-line configuration (e.g., the on-line configuration being a configuration in which the sample moves between one or more stations of the sample preparation station 20 through fluidic connections without being contained in a vessel 44, the off-line configuration being a configuration in which the sample is transported within a vessel 44 between stations of the sample preparation station 20). In embodiments that include an on-line matrix interference removal station, the analyte-containing prepared sample may flow directly from the matrix interference removal station to the next station, such as through tubing. This second station may include, for example, a second matrix interference removal station (not shown). In embodiments that include an off-line matrix interference removal station, the analyte-containing prepared sample is collected from the matrix interference removal station and placed into a vessel 58 if not already contained in a vessel 44.

The matrix interference removal station is operable to separate one or more of residual proteins, phospholipids, salts, metabolites, carbohydrates, nucleic acids, and/or other substances that may otherwise interfere with subsequent processing or analysis of the desired analytes and prior to transferring the now prepared sample to the sample analysis station 24. In some embodiments, the matrix interference removal station separates contaminants from the analyte-containing prepared sample, or more simply, the "prepared sample" (for example, by separating precipitated solids from a resulting supernatant liquid, wherein the supernatant liquid forms the prepared sample). The matrix interference removal station may include, for example, one or more of a phase separation station (not shown), a centrifuge (illustrated as reference number 76 in FIG. 2A and reference number 76' in FIG. 2B), a sonicator (not shown), a heating station (not shown), a flash freeze station (not shown), an affinity purification station (not shown), or a filtration station (not shown).

In still other embodiments, the matrix interference removal station may include an affinity extraction or purification station, for example, an immunoaffinity extraction or purification system. An exemplary immunoaffinity system may use a Mass Spectrometry Immunoassay ("MSIA") antibody enriched substrate, such as the commercially-available MSIA substrate from Intrinsic Bioprobes Inc. (Tempe, Ariz.) and that is described in U.S. Pat. No. 6,783,672, the disclosure of which is incorporated herein in its entirety. Alternatively still, the matrix interference removal station may, in yet other embodiments, include additional techniques known in the art of chemical separation, such as liquid-liquid extraction, solid phase supported liquid extraction, random access media column extraction, monolithic column extraction, dialysis extraction, dispersive solid phase extraction, solid phase micro-extraction, immunoaffinity extraction, and size exclusion using membrane filters with gravity, vacuum, or centrifugation. Many of these techniques may be practiced off-line or on-line, as appropriate, if fluid connections are created between subsequent steps of the method. Additionally, many of these techniques may be practiced in a variety of formats including, for example, using a column or cartridge format, using a pipette tip format, using a magnetic bead format, or using a plate or chip format.

Embodiments of the system 10 that include a phase separation component may include an on- or off-line solid phase extraction station (not shown) having a vacuum and/or positive pressure source (not shown) to assist in moving the sample through a solid phase extraction matrix. The solid phase extraction matrix, in turn, may include one or more suitable porous stationary phase material layers. According to one embodiment, the solid phase extraction matrix (not shown) further includes one or more filters arranged on one or both sides of the porous stationary phase material. The solid phase extraction matrix may be arranged, for example, within a column, cartridge, a pipette tip, or in a plate or chip format.

In still yet another embodiment, the matrix interference removal station may include two or more matrix interference removal methods in series. According to this embodiment, the first matrix interference removal station, for example a phase separation station, removes precipitated proteins while the second matrix interference removal station, for example a solid phase extraction station, removes additional residual proteins, phospholipids, and salts from the sample prior to analysis. Additional examples of combinations of matrix interference removal techniques include, but are not limited to, solid phase extraction followed by liquid-liquid extraction, phase separation followed by size exclusion affinity liquid chromatography, solid phase extraction followed by size exclusion affinity liquid chromatography, and immunoaffinity extraction prior to or following any of the aforementioned methods.

After the sample has passed through the secondary processing station 72, the prepared sample is transported via the transport assembly 50 to an analysis staging station 78. The analysis staging station 78 includes two or more vessel positions 82 (FIG. 2A) or two or more vessel rack positions 82' (FIG. 2B) for accepting vessels 44 or vessel racks 56, respectively. Each vessel position 82 may be stationary within the analysis staging station 78 such that once an individual vessel 44 is placed within a vessel position 82 of the analysis staging station 78, its position does not change but for transfer by the transport assembly 50.

When a particular prepared sample is selected for analysis, the vessel 44 containing the prepared sample is transferred via the transport assembly 50 from the analysis staging station 78 to an injector station 84. The injector station 84 may include an injector pipette assembly 86 (FIG. 4) to transfer an aliquot of the prepared sample from the vessel 44 to the sample analysis station 24. The injector pipette assembly 84 includes a pipette shaft 88 (FIG. 4) that may be constructed in a manner that is similar to the sample pipette assembly 58 that was described in detail above.

The injector station 84 may include a rotatable table 94 having a structure that is similar to the sampling station 46 and may include a vessel cap opening and closing device 96 for opening and closing a hinged lid, if present, and as shown in FIG. 2B.

As described in detail above, a sample of a specimen is prepared at the sample preparation station 20 before that prepared sample is moved to the sample analysis station 24. As such, at least some of the movable portions of the sample preparation station 20, including the sampling station 46, the transport assembly 50, the rotatable tables 94, and the injector pipette assembly 84, acting individually or in concert, may comprise a transport mechanism to transport the prepared sample from the sample preparation station 12 to the sample analysis station 14. One having ordinary skill in the art will appreciate that alternative embodiments of a transport mechanism to transport a prepared sample from a sample preparation station 12 to a sample analysis station 14 may be used without departing from the scope of embodiments of the invention. In the exemplary embodiment, the transport mechanism may comprise the injector pipette assembly 84, which removes an aliquot of the prepared sample for dispensing to the sample analysis station 24.

Turning now to the details of the sample analysis station 24, and in particular to FIGS. 2A-3B and 5, one embodiment of the sample analysis station 24 may be an LCMS system having a liquid chromatography station 102 and a mass spectrometer station 104. The liquid chromatography station 102 (referred to hereinafter as "LC station" 102) may include one, two, or more injection ports 106, 108 for accepting the aliquot of the prepared sample from the injector pipette assembly 86 for analysis. The injection ports 106, 108 may be connected on-line to one or more chromatography columns (e.g., a preparatory column 110 or an analytical column 112) for separation of the prepared sample into analytes of interest eluting at one or more elution times and a plurality of ancillary or waste eluents. As shown in the illustrative embodiments, the LC station 102 includes two separation channels, i.e., LC channels 110, 112 (a third LC channel 118 shown in phantom). Each LC channel 110, 112, 118 includes one preparatory column 114 and one analytical column 116, arranged in series. The preparatory column 114, according to some embodiments, may be a size exclusion affinity liquid chromatography column used for, in essence, matrix interference removal. The analytical column 116 may be a reversed-phase LC column for analyte isolation.

In other embodiments, the preparatory column 114 may be a conventional size exclusion column or any other liquid chromatography column that may be utilized as a matrix interference removal device.

Each of the two LC channels 114, 116 is associated upstream with a respective injector port 106, 108 and associated downstream with a single mass spectrometer 120 of the mass spectrometer station 104 in a manner that enables multiplexing or staggered sample introduction into the mass spectrometer 120 as described in detail below.

Figure 5:
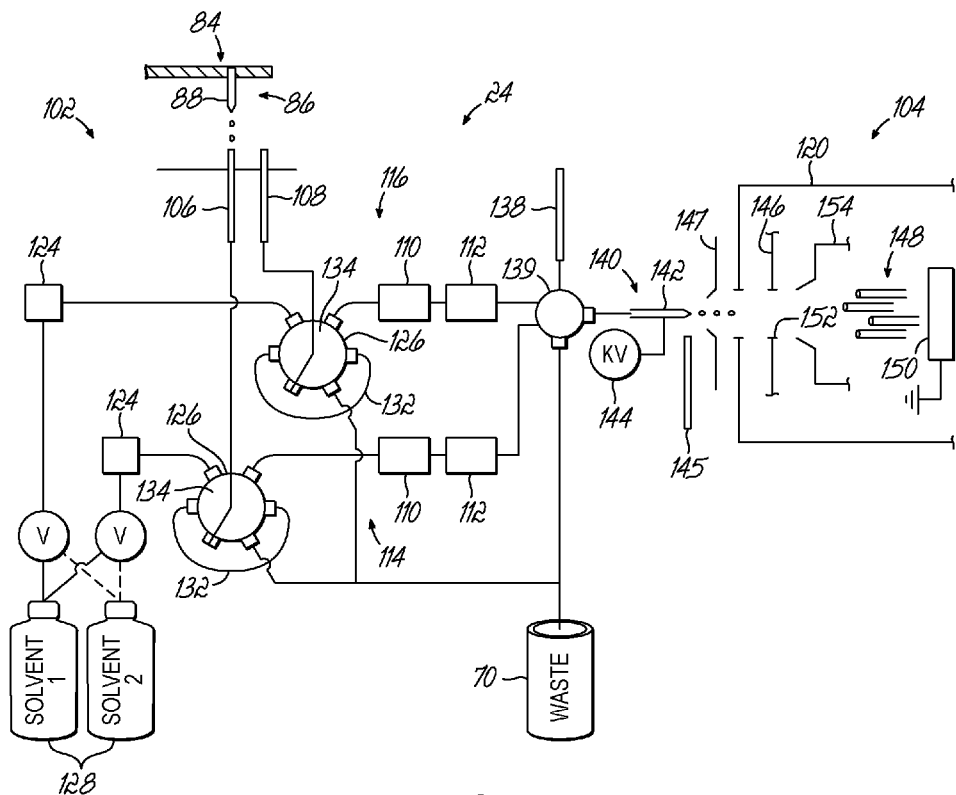
FIG. 5 is a schematic view of a sample preparation station and a sample analysis station of the automated sample preparation and analysis system of FIG. 1A in accordance with one embodiment of the present invention.

Referring still to FIG. 5, each LC channel 114, 116 may be further associated with at least one pump 124 and at least one valve 126 to control the flow of the mobile phases and the prepared sample through the sample analysis station 24.

The mobile phase is pumped to an injection valve 126 having a rotatable center 134 and six ports fluidically coupled to one injection port 106, 108 one or more of the mobile phase supplies 128, 128' (FIGS. 3A, 3B), the waste container 70, 70' (FIGS. 3A, 3B), the columns 110, 112, and a fluid loop 132 connecting Port-2 to Port-5.

The injected, prepared sample moves through the columns 110, 112 in a known manner such that at least one of the analytes of interest will elute off the columns at a retention time that differs from the retention time of other analytes of interest and/or the matrix components, i.e., eluents. The eluents and analytes from both of the first and second LC channels 114, 116 are directed into a valve 139 (which may also include an auxiliary port 138) where the eluents are directed into the waste container 70, 70' (FIGS. 3A, 3B) while the analytes are directed to an ionization source 142 of the mass spectrometer station 112. Alternative methods of sample introduction may include, but are not limited to, on-line methods (such as, flow injection analysis, direct infusion, and injection loops) and off-line methods (such as, solid phase extraction, blood spot surface coatings, matrix-assisted laser desorption/ionization ("MALDI") plate coatings, or coatings on general surfaces), may also be used to introduce the sample to the mass spectrometer 120.

As shown in FIG. 5, an atmospheric pressure ionization (either electrospray ionization ("ESI") or atmospheric pressure chemical ionization ("APCI")) device (referred to generally herein as "nebulizing ionizer") is used for ionizing the analytes received by the ionization source 140. In that regard, the nebulizing ionizer includes a capillary, probe, or needle (referred hereinafter as "needle" 142) having a solvent conduit therein (not shown) and surrounded by a gas conduit therein (not shown). An outlet of the gas conduit is positioned about 0.1 mm to about 0.2 mm proximally to an outlet of the solvent conduit. In ESI operation a voltage generator 144 is electrically coupled to the needle 142 and is operable to create a high voltage difference between the needle 142 and the counter-electrode that is either at the mass spectrometer 120.

In use, a solvent is supplied to the solvent conduit at a rate ranging from about 400 µL/min to about 2000 µL/min; however, one of ordinary skill in the art will readily appreciate that the solvent supply varies with the particular ionization source selected. The particular solvent used is dependent on the chemical nature of the analyte in study, and the methodology for selection of an appropriate solvent is well known to those of ordinary skill in the art. A gas, typically an inert gas such as N2, is supplied to the gas conduit at pressures ranging from about 0 bar to about 7 bar. The voltage generator 144 is activated and provides a voltage potential, typically ranging from about −5 kV to about 5 kV, to the solvent within the needle 142.

It would be readily appreciated that other ionization techniques are known and may be implemented as necessary or desired. For instance, ionization sources 140 suitable for ionization of liquid samples may include, for example, heated electrospray ionization ("HESI"), nanospray ionization ("NSI"), thermospray, sonic spray, atmospheric pressure photoionization ("APPI"), laser diode thermal desorption ("LDTD"), atmospheric sampling glow discharge ionization source ("ASGDI"), paperspray ionization techniques capable of extracting a specimen from a dried bloodspot, and inductively-coupled plasma ("ICP"). Ionization sources 140 that are suitable for ionization of gas samples may include, for example, chemical ionization ("CI"), electron impact ("EI"), resonance enhanced multi-photon ionization ("REMPI"), resonance multi-photon detachment ("RMPD"), glow discharge, and spark ionization. Furthermore, the ionization sources 140 for gas samples may be adapted for use with liquid samples. Ionization sources 140 that are suitable for desorbtion and ionization of a sample from a surface include, for example, MALDI, surface-assisted laser desorption/ionization ("SALDI"), surface-enhanced laser desorption/ionization ("SELDI"), desorption electrospray ionization ("DESI"), direct analysis in real time ("DART"), discontinuous atmospheric pressure interface ("DAPI"), laser diode thermal desorption ("LDTD"), and field desorption. This listing of possible ionization sources 140 is not exhaustive and may include other ionization sources and/or permutations as would be readily understood by those of ordinary skill in the art of mass spectroscopy and analytical chemistry.

A skimmer 147, positioned distal to a corona discharge electrode 145, acts in conjunction with an auxiliary gas (not shown, but directed between the outlets and the skimmer 147) to contain and/or focus the gas phase ions into a vacuum chamber of the mass spectrometer 120. The auxiliary gas may be supplied at rates that range generally from about 0 L/min to about 15 L/min.

Referring still to FIG. 5, the illustrative example of the mass spectrometer 120 includes an interface 146 with the ionization source 140, a mass filter 148, and an ion detector 150. The regions containing the mass filter 148 and the ion detector 150 are maintained under vacuum. This interface 146 includes an orifice 152 of a skimmer cone 154 that provides an opening into a higher vacuum chamber containing the mass filter 148 while maintaining vacuum pressures.

In the illustrated example, the mass filter 148 is shown to be a conventional quadrupole operating as a mass filter; however, those skilled in the art will understand the determination by which the appropriate mass filter modality for a given assay is selected. In fact, other mass spectrometer embodiments may include, for example, a single quadrupole modalities, time-of-flight ("TOF") or exactive modalities, ion trap ("OT") modalities, hybrid modalities, such as Q-TOF, TOF-TOF, Q-Exactive, LTQ-orbitrap, and LTQ-FT, or a mass spectrometer modified for proton transfer.

Still other modalities are available, and may include, for example, ion cyclotron resonance ("ICR") or magnetic sector-based analyzers. While these modalities offer high resolution and specificity, each is also very expensive. Furthermore, other detectors/analyzers may be used with, or in place of the mass spectrometer. For example, these detectors may include, for example, electrochemical devices, nuclear magnetic resonance ("NMR"), absorbance, fluorescence, refractive index, pH, and/or conductivity.

In some embodiments, the resolution of the MS technique may be enhanced by employing "tandem mass spectrometry" or "MS/MS" for example via use of a triple quadrupole mass spectrometer.

It would be readily appreciated that by incorporating the various components of the sample preparation station 12 and the sample analysis station 14 into a single system 10 may create certain contamination risks not otherwise observed in off-line systems. Therefore, the various components of these stations 12, 14 may be compartmentalized to reduce the risk of contamination between the stations 12, 14 and to permit localized abatement for contamination risks posed by specific station 12, 14.

Contamination risks include, for example, vibration, heat, electrical, liquid, and other sources of contamination common to the included components and/or automated clinical instruments. Contamination may be further reduced by including a ventilation system for each of the sample preparation station 12 and the sample analysis station 14 so as to control air flow through that station 12, 14 and to accommodate the anticipated heat generation by that station 12, 14. In similar manner, reagent storage areas, specimen storage areas, and sample storage areas may include individual refrigeration systems to maintain those portions at a lower relative temperature.

The housing 16 may be configured to have a front face 160 proximate to the user and an opposing rear face 168 (FIG. 2A), a top surface 162 positioned above a bottom surface 170 proximate to the floor, and a right-hand sidewall 164 and an opposing left-hand sidewall 166. References to terms such as "above," "upper," "below," and "lower" are for convenience of description only and represent only one possible frame of reference for describing a particular embodiment. In that regard, the system 10 is designed to include as many laboratory user touch points at or near the front face of the housing 16 as possible. For example, as depicted in FIG. 1A, each of the LC columns 110, 112, specimen racks 28, reagent racks 38, a water and/or methanol supply 122, a washing solution supply 92, the waste containers 70 buffer and mobile phase containers 128, reaction vessel plates (not shown), and disposable pipette tip plates 66 (in a tip storage station 64) are positioned at the front face of the housing 16 of the system 10 to allow easy access for replenishment and routine maintenance by the user. Similarly, those portions of the stations 12, 14 that do not require regular access by the user are positioned within the system 10 space away from the front face of the system 10. For example, LC pumps 124, power supplies 162, and controllers 21, 23 may be positioned within the housing 16 and spaced away from those components that are placed for easy access, generally referred to as "serviceable components."

Also, those components that may require attention by a service technician providing service to the system 10 are positioned to provide accessible, if not optimally convenient, access. For example, the LC pumps 124, which may require access by the service technician, may be positioned behind the waste containers 70 such that the serviceable component waste containers 70 may be removed to service the LC pumps 124.

Further, the laboratory user touch points are designed with a preference for the front face of the system 10, rather than the side of the system 10, to reduce the system footprint in the laboratory environment; if the laboratory user does not require regular access to the side of the system 10, the laboratory can pack other instruments closer to the system 10.

One of ordinary skill in the art will readily appreciate that incorporation of the centrifuge 76 into an integral housing with the analytical instrumentation of the system 10 may cause undesirable interference with those analytical instruments. In this integral configuration example, the ability of the analytical instruments to perform with a particular reliability may be compromised. This may be due to, at least in part, the high rotational speed required to draw down the precipitating solids from the supernatant liquid. Therefore, it may be necessary for embodiments of the system 10 including an integrated centrifuge 76 to further include features that reduce transmission of vibrations thereof to other components of the system 10. Moreover, because of the desire to reduce the overall footprint of the system 10, the overall size of the centrifuge 76 may be reduced and/or configured to be a standalone centrifuge 76 that is not integral with other components of the system 10, but yet accessible by the transport assembly 50.

Figure 3A:
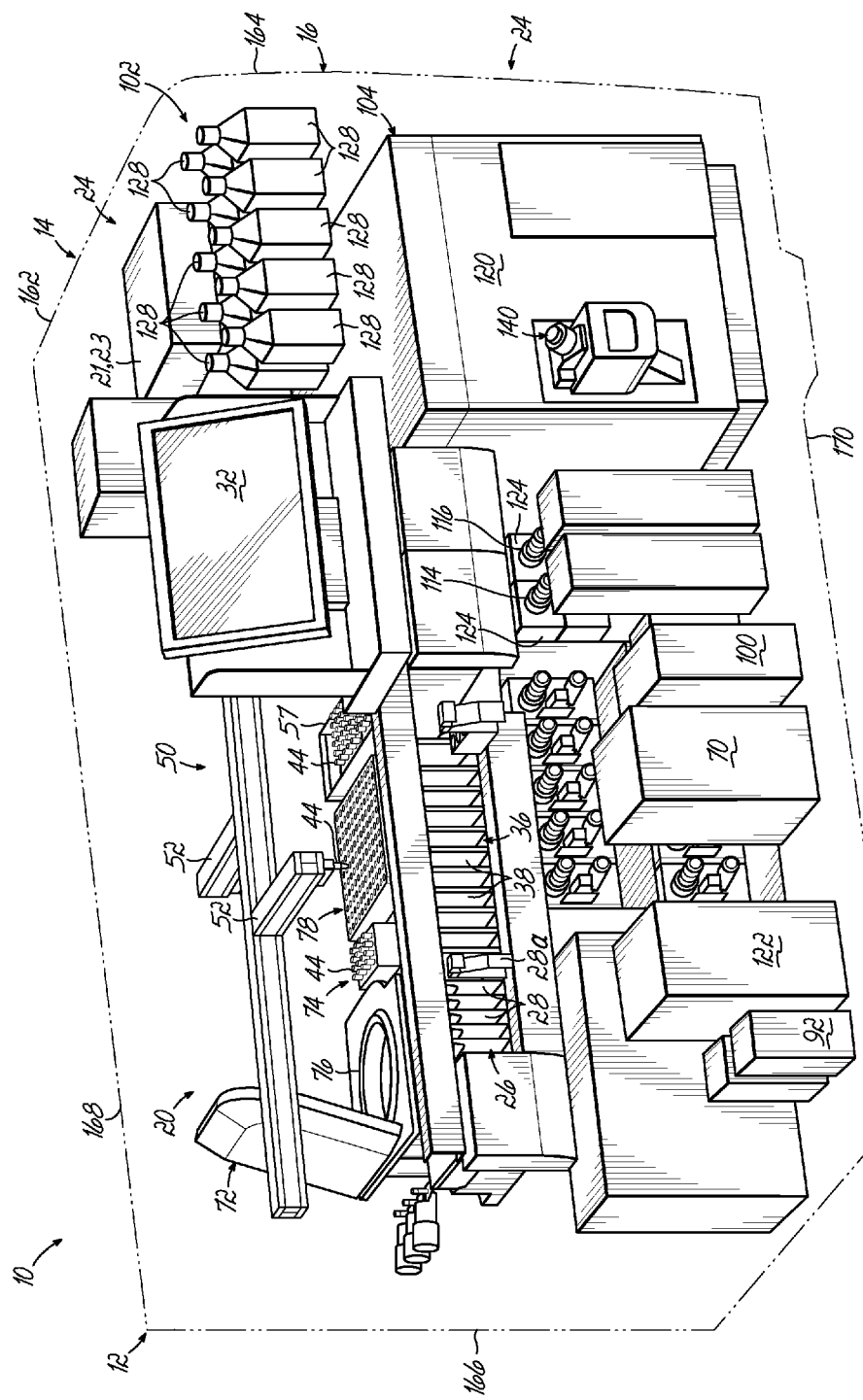
FIG. 3A is a side elevational view of the automated sample preparation and analysis system of FIG. 1A with the front cover removed.
Figure 3B:
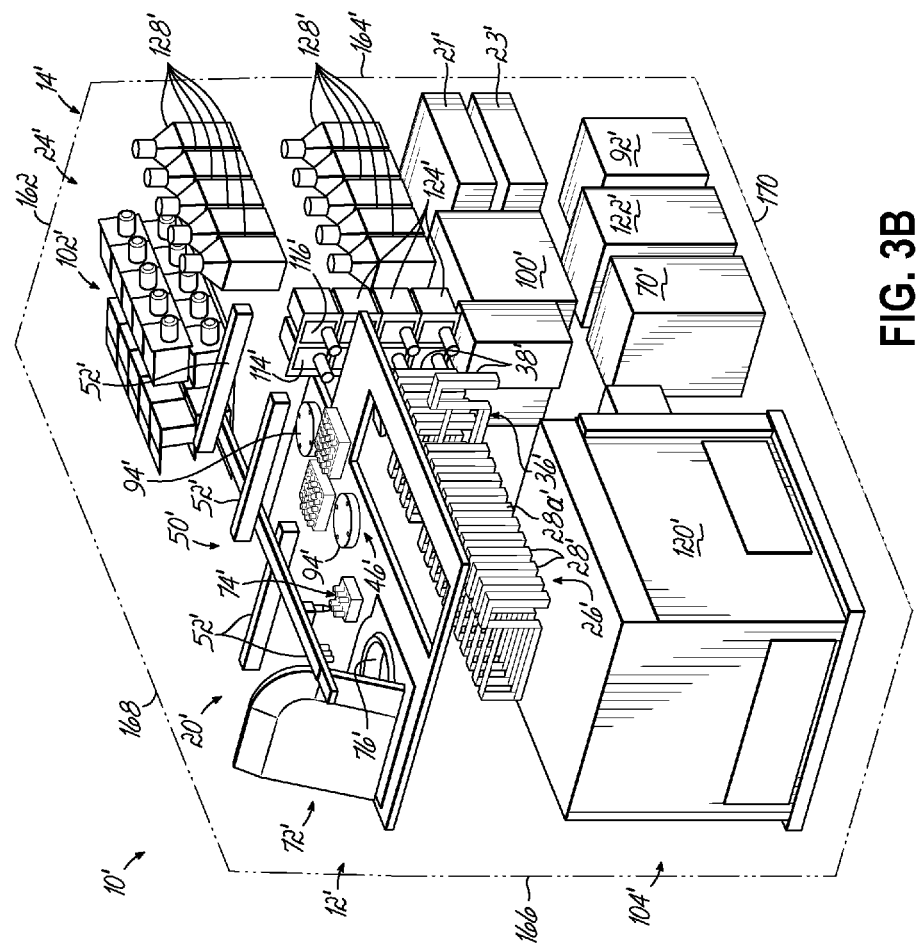
FIG. 3B is a side elevational view of the automated sample preparation and analysis system of FIG. 1B with the front cover removed.

The mobile phase reagents 128 that feed the LC pumps 124 may be positioned above the LC pumps 124. As depicted in FIGS. 3A and 3B, the mobile phase reagents 128 are positioned in the upper right quadrant of the system 10. Positioning the mobile phases above the LC pumps 124 and valves permits gravity to assist the feed of liquid mobile phase reagents 128, which results in easier priming of the LC tubing and the creation of fewer bubbles in the LC lines as compared to placing the mobile phase reagents 128 adjacent or below the LC pumps 124. Also, the mobile phase reagents 128 may be positioned near the front face of the instrument and at a height that falls approximately between the shoulders and waist of the average user.

According to one embodiment, the mass spectrometer 120 is positioned in the lower portion of the instrument. Because the mass spectrometer 120 is relatively heavy, placing the mass spectrometer 120 in a lower position improves the balance and stability of the overall system 10. More specifically, as depicted in FIGS. 3A-3B, the mass spectrometer 120 is positioned in the lower right quadrant of the system 10.

The mass spectrometer 120 is positioned on a support that is moveable horizontally with respect to the housing, for example, a sliding drawer, capable of moving the mass spectrometer into and out of the system footprint. Placing the mass spectrometer 120 on a drawer provides several benefits, including improved access to all sides of the instrument for routine maintenance and servicing, improved manufacturing efficiency by permitting the mass spectrometer 120 to be installed onto the drawer and then slidingly inserted into the housing 16, eliminating the step of inserting a bulky and heavy component within a restricted space inside the housing 16, and relative isolation of the sensitive mass spectrometer 120 from vibrational, thermal, electrical, liquid and other contamination emanating from other components of the system 10.

The serviceable components of the mass spectrometer 120 are positioned on the front face of the mass spectrometer 120 or on the top of the mass spectrometer 120, rather than on or near the rear of the mass spectrometer 120. Serviceable components include, but are not limited to, the ionization source 140. However, due to its size and shape, placing the ionization source 140 on the front of the mass spectrometer 120 creates a protrusion on the front of the system 10, extending beyond the front plane of the housing 16. Therefore, the ionization source 140 is designed to be removed during system transport and installed onto the mass spectrometer 120 during installation of the system 10 within the laboratory environment.

Due to the relative height of the mass spectrometer 120, and also due to the relative height of the sample preparation station 12, it is preferred that the mass spectrometer 120 is positioned in a quadrant of the system 10 opposite from the sample preparation station 12. For example, as depicted in FIG. 3A, the mass spectrometer 120 is positioned in the right quadrant and at a lower height as compared to the sample preparation station 12, which is positioned in the left quadrant and at a higher height than the mass spectrometer 120 of the system 10; however, in FIG. 3B, both the mass spectrometer 120' and the sample preparation station 12' are positioned in the left half of the system 10'. Additionally, due to the possibility of vibrational and liquid contamination emanating from the sample preparation station 12, which contamination may interfere with the operational precision of the mass spectrometer 120, it is preferred that the sample preparation station 12 is located not directly above the mass spectrometer 120.

Also in consideration for the relative height of the mass spectrometer 120, and for the relative height of the LC pumps 124, it is preferred that the LC pumps 124 are positioned not directly above the mass spectrometer 120. However, the mass spectrometer 120 is preferably positioned relatively close to the LC pumps 124, which LC pumps 124 are located in the central lower portion of the overall system 10, as depicted in FIG. 3A-3B. Placing the LC pumps 124 relatively close to the mass spectrometer 120 is important to minimize, as much as possible, the distance of the fluidic connections between the LC pumps 124 and the mass spectrometer 120, which thereby reduces the liquid dead volume in the LC system lines and also reduces the risk of degradation of the chromatography caused by the separated liquid traveling over a distance.

While most of the system components are located within the housing 16, one or more components may optionally be located remotely from the system 10, either adjacent to the system 10 or at some distance from the system 10, but integrated into the system 10 using tubing or the like. For example, mechanical pumps, including roughing pumps, a nitrogen generator or other inert gas sources for operation of the mass spectrometer 120 may be located in a separate frame or frames. Due to their thermal output, as well as their noise and vibration, placement of these components within the housing 16 is not advantageous. While these components could be integrated within the housing 16, they also can be located remotely without denigrating system performance. Having the option to locate these components remotely, for example, in another location within the same laboratory environment, or even in an adjacent room within the overall laboratory, provides significant installation flexibility for the laboratory operator.

While the present invention has been illustrated by a description of various embodiments, and while these embodiments have been described in some detail, they are not intended to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with methods of practicing the present invention as currently known. However, the invention itself should only be defined by the appended claims.

What is claimed is:

1. A sample preparation and analysis system, comprising:
   a housing;
   a sample preparation station comprising a centrifuge positioned within the housing;
   a sample analysis station comprising a mass spectrometer positioned within the housing and interconnected in an automated manner with the sample preparation station; and
   a transport assembly configured to move at least one sample within the housing in an automated manner between the sample preparation station and the sample analysis station,
   wherein the mass spectrometer is contained within a sliding drawer within the housing in the lower portion of the system.

2. The sample preparation and analysis system of claim 1, wherein the sample preparation station is positioned substantially on one side of the housing, at a height that is greater than a height of a base of an analyzer included in the sample analysis station; and
   the analyzer is positioned substantially on the other side of the housing, at a height that is less than a height of a base of the sample preparation station.

3. The sample preparation and analysis system of claim 1, wherein the sample analysis station further includes one or more liquid chromatography pumps and at least one liquid chromatography mobile phase container, the at least one liquid chromatography mobile phase container being positioned at a height that is greater than a height of the one or more liquid chromatography pumps.

4. The sample preparation and analysis system of claim 1, wherein the sample analysis station further includes an analyzer selected from the group consisting of a liquid chromatograph directly coupled to the mass spectrometer, a gas chromatograph directly coupled to the mass spectrometer, a surface desorption/ionizer directly coupled to the mass spectrometer, a liquid chromatography ultra-violet spectrometer, and a fluorescence spectrometer.

5. The sample preparation and analysis system of claim 1, wherein the sample preparation station includes at least one of a specimen dock having one or more specimen racks capable of holding a specimen container and a reagent station having one or more reagent racks capable of holding one or more reagent containers.

6. The sample preparation and analysis system of claim 1, further comprising a user interface, wherein the user interface is located centrally along the overall length of the housing between a left-hand sidewall of the housing and a right-hand sidewall of the housing.

7. The sample preparation and analysis system of claim 1, wherein the transport assembly is configured to move the sample in at least one of an x-y direction, an x-y-z direction, or a rotary direction.

8. The sample preparation and analysis system of claim 1, wherein the transport assembly includes a sample pipette assembly.

9. The sample preparation and analysis system of claim 1 further comprising a secondary processing station that includes one or more of a mixing station, an incubation station, and a matrix interference removal station and wherein the transport assembly is configured to move the at least one sample between the sample preparation station, the secondary processing station, and the sample analysis station.

10. The sample preparation and analysis system of claim 1 further comprising an injector station positioned in the housing, wherein the injection station is configured to receive a sample prepared from the transport assembly and transfer an aliquot of the sample to the sample analysis station.

11. A sample preparation and analysis system, comprising:
    a housing;
    a sample preparation station positioned within the housing and configured to prepare a sample taken from a specimen in accordance with an assay selected from a database containing a plurality of unique assays;
    a sample analysis station positioned within the housing and spaced away from the sample preparation station, the sample analysis station comprising an analyzer comprising a mass spectrometer, the analyzer being dynamically reconfigurable in response to the selected assay to analyze the prepared sample in accordance with the selected assay; and
    a transport mechanism including a rotatable table configured to transport a vial containing the prepared sample within the housing and from the sample preparation station to the sample analysis station.

12. The sample preparation and analysis system of claim 11, wherein the sample preparation station is positioned substantially on one side of the housing, at a height that is greater than a height of a base of an analyzer included in the sample analysis station; and the analyzer is positioned substantially on the other side of the housing, at a height that is less than a height of a base of the sample preparation station.

13. The sample preparation and analysis system of claim 11, wherein the sample analysis station further includes one or more liquid chromatography pumps and at least one liquid chromatography mobile phase container, the at least one liquid chromatography mobile phase container being positioned at a height that is greater than a height of the one or more liquid chromatography pumps.

14. The sample preparation and analysis system of claim 11, wherein the sample preparation station includes at least one of a specimen dock having one or more specimen racks capable of holding a specimen container and a reagent station having one or more reagent racks capable of holding one or more reagent containers.

15. The sample preparation and analysis system of claim 11 further comprising a user interface, wherein the user interface is located centrally along the overall length of the housing between a left-hand sidewall of the housing and a right-hand sidewall of the housing.

16. The sample preparation and analysis system of claim 11, wherein the sample analysis station further includes an analyzer selected from the group consisting of a liquid chromatograph directly coupled to the mass spectrometer, a gas chromatograph directly coupled to the mass spectrometer, a surface desorption/ionizer directly coupled to the mass spectrometer, a liquid chromatography ultra-violet spectrometer, a fluorescence spectrometer, and combinations thereof.

17. The sample preparation and analysis system of claim 11, wherein the transport mechanism further includes at least one of a transport assembly, an injector pipette assembly, a fluidic coupler, or combinations thereof.

18. The sample preparation and analysis system of claim 17, wherein the transport assembly is configured to move the sample in at least one of an x-y direction, an x-y-z direction, or a rotary direction.

19. The sample preparation and analysis system of claim 11, further comprising a secondary processing station that includes one or more of a mixing station, an incubation station, and a matrix interference removal station and wherein the transport mechanism is configured to transport the prepared sample within the housing and from the sample preparation station to the sample analysis station, from the sample preparation station to the secondary processing station and from the secondary processing station to the sample analysis station.

20. An automated biological specimen preparation and mass spectrometry analysis system for analyzing a plurality of biological specimens, comprising:

a sample preparation station configured to prepare samples taken from the plurality of biological specimens;

a secondary processing station configured to receive samples from the sample preparation station and including one or more of a mixing station, an incubation station, and a matrix interference removal station; and a sample analysis station including a mass spectrometer configured to receive samples from the secondary processing station and to quantify one or more analytes in one or more of the processed samples;

wherein the sample preparation station and the sample analysis station are contained within a housing and such that the mass spectrometer is positioned at a height that is lower than a height of the sample preparation station;

wherein the mass spectrometer is contained within a sliding drawer within the housing.

* * * * *